(12) United States Patent
Rowe

(10) Patent No.: US 10,060,258 B2
(45) Date of Patent: Aug. 28, 2018

(54) SYSTEMS AND METHODS FOR OPTIMIZING ANALYSIS OF SUBTERRANEAN WELL BORES AND FLUIDS USING NOBLE GASES

(71) Applicant: Halliburton Energy Services, Inc., Houston, TX (US)

(72) Inventor: Mathew Rowe, Lafayette, LA (US)

(73) Assignee: Halliburton Energy Services, Inc., Houston, TX (US)

( * ) Notice: Subject to any disclaimer, the term of this patent is extended or adjusted under 35 U.S.C. 154(b) by 331 days.

(21) Appl. No.: 14/767,452

(22) PCT Filed: Mar. 8, 2013

(86) PCT No.: PCT/US2013/029924
§ 371 (c)(1),
(2) Date: Aug. 12, 2015

(87) PCT Pub. No.: WO2014/137356
PCT Pub. Date: Sep. 12, 2014

(65) Prior Publication Data
US 2015/0361792 A1   Dec. 17, 2015

(51) Int. Cl.
*E21B 49/08* (2006.01)
*E21B 47/10* (2012.01)
(Continued)

(52) U.S. Cl.
CPC .......... *E21B 49/08* (2013.01); *E21B 47/0003* (2013.01); *E21B 47/1015* (2013.01);
(Continued)

(58) Field of Classification Search
CPC ..... E21B 47/0003; E21B 49/008; E21B 49/08
See application file for complete search history.

(56) References Cited

U.S. PATENT DOCUMENTS

| | | | | |
|---|---|---|---|---|
| 4,246,965 A | * | 1/1981 | Cha | E21B 43/247 166/250.15 |
| 4,887,464 A | * | 12/1989 | Tannenbaum | E21B 21/08 175/206 |

(Continued)

FOREIGN PATENT DOCUMENTS

WO     02/50398 A1    6/2002
WO   2011/047236 A1   4/2011

OTHER PUBLICATIONS

International Search Report and Written Opinion issued in related PCT Application No. PCT/US2013/029924 dated Nov. 15, 2013, 12 pages.
International Preliminary Report on Patentability issued in related PCT Application No. PCT/US2013/029924, dated Sep. 17, 2015 (9 pages).

*Primary Examiner* — Evan Pert
(74) *Attorney, Agent, or Firm* — John Wustenberg; Baker Botts L.L.P.

(57) ABSTRACT

Systems and methods for monitoring and characterizing fluids in subterranean formations are provided. In one embodiment, a method for monitoring a well bore is provided, the method including: providing a first quantity of one or more noble gases of a known volume; circulating at least a portion of the fluid and the one or more noble gases in a portion of the well bore; detecting a second quantity of the noble gases in a portion of the fluid that has been circulated in a portion of the well bore; and determining one or more parameters relating to the well bore (e.g., well bore volume, lag time, flow characteristics, and/or efficiency of a gas extraction system) based on the quantities of the noble gases provided and/or detected in the fluid and/or the relative times at which the noble gases are provided or detected.

20 Claims, 1 Drawing Sheet

(51) Int. Cl.
*E21B 49/00* (2006.01)
*E21B 47/00* (2012.01)
*G01N 33/24* (2006.01)

(52) U.S. Cl.
CPC .......... *E21B 49/005* (2013.01); *E21B 49/008* (2013.01); *G01N 33/241* (2013.01)

(56) References Cited

U.S. PATENT DOCUMENTS

| | | | | |
|---|---|---|---|---|
| 5,273,781 | A | * | 12/1993 | Shu ...................... D06N 3/0059 160/236 |
| 5,277,263 | A | | 1/1994 | Amen |
| 5,501,273 | A | * | 3/1996 | Puri ...................... E21B 43/006 166/245 |
| 6,585,044 | B2 | * | 7/2003 | Rester ...................... E21B 47/10 166/187 |
| 8,132,452 | B1 | | 3/2012 | Selman et al. |
| 2005/0252286 | A1 | * | 11/2005 | Ibrahim ............. G01N 33/2823 73/152.55 |
| 2011/0277996 | A1 | * | 11/2011 | Cullick ................. E21B 33/138 166/250.12 |
| 2012/0134749 | A1 | * | 5/2012 | Darrah ............... E21B 47/1015 405/80 |
| 2012/0234599 | A1 | * | 9/2012 | Brumboiu ............... E21B 21/01 175/50 |
| 2014/0250999 | A1 | * | 9/2014 | Lawson .............. E21B 47/1015 73/152.23 |

* cited by examiner

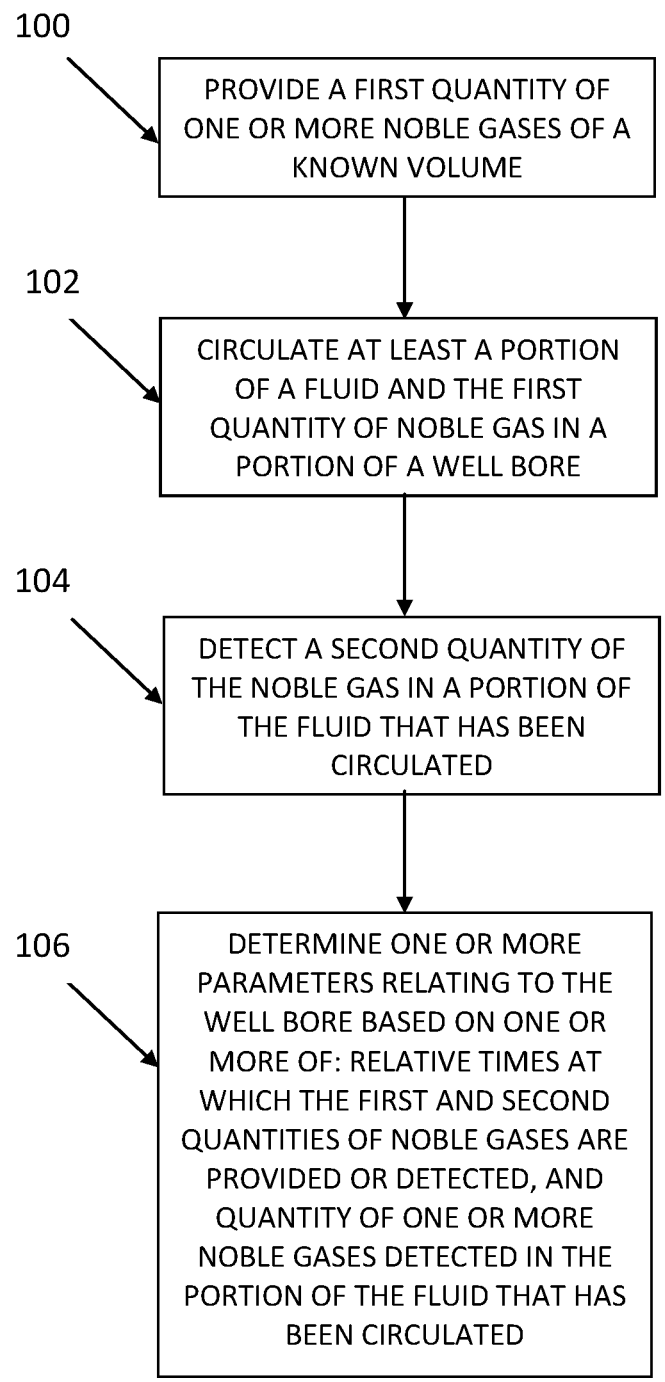

ial Stage Appli-
SYSTEMS AND METHODS FOR OPTIMIZING ANALYSIS OF SUBTERRANEAN WELL BORES AND FLUIDS USING NOBLE GASES

CROSS-REFERENCE TO RELATED APPLICATION

The present application is a U.S. National Stage Application of International Application No. PCT/US2013/029924 filed Mar. 8, 2013, which is incorporated herein by reference in its entirety for all purposes.

BACKGROUND

The present disclosure relates to subterranean operations and, more particularly, to systems and methods for monitoring and characterizing well bores and fluids in a subterranean formation.

Performance of subterranean operations entails various steps, each using a number of devices. Many subterranean operations entail introducing one or more fluids into the subterranean formation. For instance, drilling operations play an important role when developing oil, gas or water wells or when mining for minerals and the like. During the drilling operations, a drill bit passes through various layers of earth strata as it descends to a desired depth. Drilling fluids are commonly employed during the drilling operations and perform several important functions including, but not limited to, removing the cuttings from the well to the surface, controlling formation pressures, sealing permeable formations, minimizing formation damage, and cooling and lubricating the drill bit.

Properties of the drilling fluid are typically monitored during drilling operations. For instance, it is often desirable to accurately measure hydrocarbon gas concentrations of the drilling fluid as it leaves the well bore. The level of the hydrocarbon gas in the drilling fluid may affect how the well is to be drilled as well as the safety of the drilling rig and personnel involved. Moreover, the concentration of hydrocarbon gases and other components present in the drilling fluid may be indicative of the characteristics of the formation being drilled and the drilling environment. Accordingly, the analysis of drilling fluids and the changes they undergo during drilling operations may be important to the methods of drilling as well as the efficiency of the drilling operations. Consequently, during drilling, completion and testing of a wellbore, it is desirable to obtain analytical measurements of the fluids that are returned to the surface from the well bore.

One proposed method for collecting and analyzing the drilling fluid involves submerging a rotor within a vessel into the drilling fluid as the drilling fluid exits the wellbore. Typically, the placement of this "gas trap" is in an open pit or header box which is exposed to atmospheric conditions. The drilling fluid is agitated as it enters into and exits out of the vessel and some of the gasses dissolved therein evaporate and escape the confines of the fluid. These vaporized gases are then collected and processed by analytical methods to determine the presence and levels of hydrocarbons and other components in the drilling fluid.

There are currently various conventional methods for collection of gaseous samples for analytical processing during drilling operations. One method entails attaching the sample point to the primary fluid/gas separator near the atmospheric end of the manifold system. However, by the time the gas from the well bore has entered the large volume of this separator it has typically become less significant as it has already undergone mixing with other gases and lag separation from the fluids from which it was derived. Other methods entail collecting an amount of drilling fluid before the separator and processing the drilling fluid to extract any gaseous compounds that are dissolved therein. Because the sampling in the second method occurs in the main stream of fluid from the well, it will not be compromised by the mixing of any other atmospheric gases or be separated from lag by any other process. However, this method does not allow an efficient continuous sampling of the drilling fluids.

Thus, most method for collection of gaseous samples for analytical processing during drilling operations generally require some way of accounting for lag time in the well bore and efficiency of the sampling method in order to provide accurate information regarding the composition and location hydrocarbons and other fluids downhole. Conventional methods may utilize standard correction factors to account for efficiency of the gas extractor; however, such correction factors may not accurately reflect the efficiency of a particular system.

BRIEF DESCRIPTION OF THE DRAWING

FIG. 1 is a process flow diagram illustrating a method for monitoring a well bore and/or determining the efficiency of a gas extraction system, in accordance with an embodiment of the present disclosure.

DETAILED DESCRIPTION

Illustrative embodiments of the present disclosure are described in detail herein. In the interest of clarity, not all features of an actual implementation may be described in this specification. It will of course be appreciated that in the development of any such actual embodiment, numerous implementation-specific decisions may be made to achieve the specific implementation goals, which may vary from one implementation to another. Moreover, it will be appreciated that such a development effort might be complex and time-consuming, but would nevertheless be a routine undertaking for those of ordinary skill in the art having the benefit of the present disclosure.

For purposes of this disclosure, an information handling system may include any instrumentality or aggregate of instrumentalities operable to compute, classify, process, transmit, receive, retrieve, originate, switch, store, display, manifest, detect, record, reproduce, handle, or utilize any form of information, intelligence, or data for business, scientific, control, or other purposes. For example, an information handling system may be a personal computer or tablet device, a cellular telephone, a network storage device, or any other suitable device and may vary in size, shape, performance, functionality, and price. The information handling system may include random access memory (RAM), one or more processing resources such as a central processing unit (CPU) or hardware or software control logic, ROM, and/or other types of nonvolatile memory. Additional components of the information handling system may include one or more disk drives, one or more network ports for communication with external devices as well as various input and output (I/O) devices, such as a keyboard, a mouse, and a video display. The information handling system may also include one or more buses operable to transmit communications between the various hardware components.

For the purposes of this disclosure, computer-readable media may include any instrumentality or aggregation of instrumentalities that may retain data and/or instructions for a period of time. Computer-readable media may include, for example, without limitation, storage media such as a direct access storage device (e.g., a hard disk drive or floppy disk drive), a sequential access storage device (e.g., a tape disk drive), compact disk, CD-ROM, DVD, RAM, ROM, electrically erasable programmable read-only memory (EEPROM), and/or flash memory; as well as communications media such wires, optical fibers, microwaves, radio waves, and other electromagnetic and/or optical carriers; and/or any combination of the foregoing.

The terms "couple" or "couples," as used herein are intended to mean either an indirect or a direct connection. Thus, if a first device couples to a second device, that connection may be through a direct connection, or through an indirect electrical connection via other devices and connections. The term "communicatively coupled" as used herein is intended to mean coupling of components in a way to permit communication of information therebetween. Two components may be communicatively coupled through a wired or wireless communication network, including but not limited to Ethernet, LAN, fiber optics, radio, microwaves, satellite, and the like. Operation and use of such communication networks is well known to those of ordinary skill in the art and will, therefore, not be discussed in detail herein.

It will be understood that the term "oil well drilling equipment" or "oil well drilling system" is not intended to limit the use of the equipment and processes described with those terms to drilling an oil well. The terms also encompass drilling natural gas wells or hydrocarbon wells in general. Further, such wells can be used for production, monitoring, or injection in relation to the recovery of hydrocarbons or other materials from the subsurface. This could also include geothermal wells intended to provide a source of heat energy instead of hydrocarbons.

The present disclosure relates to subterranean operations and, more particularly, to systems and methods for monitoring and characterizing well bores and fluids in a subterranean formation.

The systems and methods of the present disclosure generally involve providing a known volume of one or more noble gases (e.g., helium, neon, argon, krypton, xenon, or radon) at a known pressure and one or more fluids (e.g., drilling fluids) that are circulated into the well bore. The one or more fluids are then circulated out of the well bore, and a portion of those fluids are extracted for analysis. The amount of the noble gas detected in the fluid sample may be used to calculate, among other parameters, the total volume of the well bore, the efficiency of the gas trap, and/or the lag time in the well bore.

In certain embodiments of the present disclosure, the known volume of one or more noble gases at a known pressure is introduced into the well bore. This may be accomplished by inserting a gas injection apparatus into fluid communication with one of the fluid lines feeding one or more fluids (e.g., drilling fluids) into the well bore via one or more pumps. The gas injection apparatus may be operated manually or by an automated system, either in whole or in part. One such apparatus may include a basic pressure valve. Other apparatus may include cylinders, pistons, and/or other apparatus that are capable of injecting gases at a controlled pressure. A person of skill in the art with the benefit of this disclosure will recognize appropriate gas injection apparatus for use in a particular application of the present invention. The time at which the noble gas is introduced into the well bore ($t_i$) may be recorded for use in subsequent analysis, including certain methods of the present disclosure. In certain embodiments, the gas injection apparatus may further include one or more sensors that are configured to detect the injection of gas and the amount of gas injected into the fluid lines. These sensors may be communicatively coupled to a control system and/or information handling system that, among other things, uses data from those sensors to perform calculations in the methods of the present disclosure as described below.

The one or more noble gases may include a single noble gas, or it may include any mixture of any of such gases. Any known volume of noble gas may be used that is suitable for the particular application of the methods of the present disclosure. In certain embodiments, the volume of noble gas may be from about 5 liters to about 50 liters. The amount and/or composition of the noble gases used in a particular embodiment of the present disclosure may depend on numerous factors that will be apparent to a person of skill in the art with the benefit of this disclosure, including but not limited to compatibility with the fluids present in the well bore and/or subterranean formation, atmospheric conditions at the surface, and other factors.

In certain embodiments, one or more fluid measurement devices that are configured to detect volumes and/or flow rates of one or more fluids introduced into or exiting the well bore may be positioned along one or more of the fluid lines feeding one or more fluids (e.g., drilling fluids) into the well bore. These fluid measurement devices may include any type of sensor device known in the art capable of monitoring fluid volume or flow, including but not limited to acoustic sensors, nuclear sensors, coriolis meters, doppler radar, vortex flow meters or sensors, calorimetric flow meters or sensors, magnetic flow meters or sensors, electromagnetic meters or sensors, differential pressure meters or sensors, open channel meters or sensors, and the like. These fluid measurement devices may be communicatively coupled to a control system and/or information handling system that, among other things, uses data from those sensors to perform calculations in the methods of the present disclosure as described below.

A desired amount of a fluid including the one or more noble gases may be directed to a gas extraction system upon exiting the well bore. The gas extraction system may be any system suitable for extracting a gaseous sample from the fluid sample. The extraction system may include a fluid gas extraction system for extracting any gases dissolved in the fluid. In one exemplary embodiment, the fluid gas extraction system may be the EAGLE™ or CVE™ gas extraction systems available from Halliburton Energy Services of Duncan, Okla. The extraction system may liberate and extract dissolved gases from drilling fluids in a controlled manner. The extraction system also may purge the sample with nitrogen or another inert gas in order to substantially remove noble gases from the atmosphere that have become dissolved into the sample. The collected gases may then be directed to a gaseous sample outlet and delivered to an one or an array of analyzers for processing. In one embodiment, the extraction system may include one or more pumps for transporting the drilling fluid sample through the extraction process and returning the drilling fluid sample to the rig at the outlet of the extraction system. The extraction system may further include a heater for regulating the temperature of the drilling fluid sample and a degasser for providing a sealed method of liberating and separating dissolved gases from the drilling fluid sample and collecting these gasses for analysis while displacing the spent liquid to be returned to the rig through the outlet. The extraction system may further include a cooler for cooling the sample gas prior to analysis and sensors that allow the process to be continuously measured. The operations of the extraction system are well known to one of ordinary skill in the art and will therefore not be discussed in detail herein.

A gas analyzer may be coupled to the gas extraction system, integrally formed with the extraction system, or may be located in another place, building, unit or work area, separate from the extraction system. In this embodiment, the gas extracted from the fluid by the extraction system may be directed to a gas analyzer through a gaseous sample outlet. Gas analyzers are well known to those of ordinary skill in the art and will therefore not be discussed in detail herein. The gas analyzers may be used to analyze the gas sample extracted from the fluid sample and, in particular, detect the noble gas that was introduced into the system when it is circulated out of the well bore. That analysis may be used to provide desirable information such as, for example, information regarding the formation in which the fluids and noble gases have been circulated.

In certain embodiments, the shape of the peak of the detected noble gas in one or more fluid samples taken from the well may indicate various types of phenomena or activity downhole, such as washouts, drilling fluid loss, production of formation fluids, flow characteristics, and the like. For example, if all or substantially all of the noble gas introduced into the well bore is detected in fluid samples taken from the well bore over a continuous, relatively short period of time, this may indicate substantially laminar flow and/or a lack of turbulent flow in the well bore. Conversely, if the noble gas introduced into the well bore is detected in fluid samples taken over a longer period of time, or if the noble gas is detected only intermittently in fluid samples taken, this may indicate the presence of turbulent flow (e.g., formation fluids entering the well bore) that have caused the volume of noble gas to become divided into smaller volumes and/or dispersed throughout a larger volume of fluid. Because amount of noble gas introduced into the well bore and the time at which it was introduced are known, the amount of noble gas detected and the time at which it is detected exiting the well bore also may be used to calculate various well bore parameters.

For example, the detection of noble gas in the fluid sample may be used to calculate the total volume of the well bore. First, the total volume of the well bore is equal to the total amount of fluid pumped into the well bore ($V_P$), which can be expressed according to Equation (1) below.

$$V_P = F(t_d - t_i) \quad (1)$$

wherein F is the average flow rate through the well bore, $t_d$ is the time at which a particular fluid (i.e., the noble gas) is detected in the gas analyzer. The total volume of the well bore can also be expressed as the sum of the following volumes: (1) the volume ($V_s$) of the surface piping that runs from the injection site into the drill pipe, (2) the volume ($V_D$) of the drill pipe present in the well bore, (3) the volume ($V_C$) inside the casing (that consists of n pieces of casing) in the well bore, and the open hole volume ($V_o$). Values for $V_s$, $V_D$, and $V_C$ can be calculated based on a set of parameters having known values in a particular well. The volume ($V_s$) of the surface piping (that consists of i pieces of pipe) that runs from the injection site into the drill pipe may be calculated according to Equation (2) below:

$$V_s = \sum_i \left(\frac{D_i}{4}\right)^2 \pi \cdot L_i \quad (2)$$

wherein $D_i$ is the diameter of each piece of pipe and $L_i$ is the length of each piece of pipe. The volume ($V_D$) of the drill pipe (that consists of j pieces of drill pipe) present in the well bore may be calculated according to Equation (3) below:

$$V_D = \sum_j \left(\frac{D_j}{4}\right)^2 \pi \cdot L_j \quad (3)$$

wherein $D_j$ is the diameter of each piece of drill pipe and $L_j$ is the length of each piece of drill pipe. The volume ($V_C$) inside the casing (that consists of n pieces of casing) in the well bore may be calculated according to Equation (3) below:

$$V_C = \sum_{n,j} \left(\frac{D_n - D_j}{4}\right)^2 \pi \cdot L_n \quad (4)$$

wherein $D_n$ is the inside diameter of each piece of casing, $D_j$ is the outside diameter of the drill pipe therein, and $L_n$ is the length of each piece of casing.

The open hole diameter ($D_o$) can be expressed as a function of the various volumes discussed above, according to Equation (5) below:

$$D_o = 4\left[\frac{(V_P - V_s - V_D - V_C)}{\pi L}\right]^{1/2} + D_j \quad (5)$$

wherein $D_j$ is the outside diameter of the drill pipe and L is the depth of the hole.

Lag times in the well bore also may be calculated using the detection of the noble gas in the fluid sample. Lag time for the entire well bore ($L_w$) may be expressed as a function of the volume of fluid pumped into the well bore and the average flow rate through the well bore, according to Equation (6) below:

$$L_w = \frac{V_P}{F} \quad (6)$$

wherein F is the average flow rate through the well bore and $V_P$ is the total amount of fluid pumped into the well bore. Lag time ($L_B$) for the portion of the well bore from the bottom hole to the surface similarly may be expressed according to Equation (7) below:

$$L_B = \frac{V_P - V_D}{F} \quad (7)$$

wherein $V_D$ can be calculated according to Equation (3) above.

The amount of noble gas detected in the fluid sample also may be used to calculate the efficiency of the gas extractor. The concentration of noble gas in the fluid per unit volume is governed by the ideal gas law, and may be expressed according to Equation (8)

$$\frac{M_o}{V_o} = \frac{P}{RT} \quad (8)$$

wherein $M_o$ and $V_o$ are the initial mass and volume of the noble gas introduced, P is the initial pressure, R is the gas constant and T is the initial temperature. The area under the curve for the amount of noble gas detected in the gas analyzer over a period of time (t) may be numerically integrated to determine the total amount of the noble gas extracted ($M_t$). The total volume of fluid extracted by the gas extractor ($V_t$) may be expressed as a function of that period of time (t) according to Equation (9):

$$V_t = tF_E \quad (9)$$

wherein $F_E$ is the flow rate through the gas extractor. The efficiency (E) of the extractor can then be expressed according to Equation (10) below.

$$E = 100\left(\frac{M_t V_o}{V_t M_o}\right) \quad (10)$$

This value E may be used, among other purposes, to account for the efficiency of the gas extractor in calculating volumes of other gases detected in the fluid sample, in lieu of conventionally-used correction factors. This may, among other benefits, provide greater accuracy in assessing the composition of gases in a fluid sample and/or the composition of fluids residing in portions of a subterranean formation penetrated by the well bore.

In certain embodiments, the methods and systems of the present disclosure may facilitate calculating lag time and/or total well volume based exclusively on surface measurements. In certain embodiments, the methods and systems of the present disclosure may facilitate calculating lag time and/or total well volume and/or detecting flow characteristics in the well bore during operations in which the fluids including the noble gas are present in the well bore (i.e., substantially in or near real time). In certain embodiments, the methods and systems of the present disclosure may facilitate calculating two or more of lag time, total well volume, and/or gas trap efficiency using the same measurements at a well site. In certain embodiments, the methods and systems of the present disclosure may facilitate calculating two or more of lag time, total well volume, and/or gas trap efficiency substantially simultaneously. Thus, the methods and systems of the present disclosure may, among other benefits, provide greater efficiency in monitoring well bore activity and/or facilitate early planning of remedial, cementing, or other completion operations. The use of a noble gas may, among other benefits, provide greater operational safety and/or reduce side reactions with the sample and/or the environment as compared to other types of reference fluids or gases.

In certain embodiments, a control system may be used to collect, process and display data regarding activities at the well site (either automatically via sensors at the well site or manually entered into the system), perform calculations using that data, as described above, and/or execute instructions to perform various functions at a well site. The control system may include an information handling system, such as a programmable logic controller or PLC, a suitably programmed computer, etc. Any suitable processing application software package may be used by the control system to process the data. In one embodiment, the software produces data that may be presented to the operation personnel in a variety of visual display presentations such as a display. In certain example system, the measured value set of parameters, the expected value set of parameters, or both may be displayed to the operator using the display. For example, the measured-value set of parameters may be juxtaposed to the expected-value set of parameters using the display, allowing the user to manually identify, characterize, or locate a downhole condition. The sets may be presented to the user in a graphical format (e.g., a chart) or in a textual format (e.g., a table of values). In another example system, the display may show warnings or other information to the operator when the central monitoring system detects a downhole condition. Suitable control systems and interfaces for use in the methods and systems of the present disclosure may include SENTRY™ and INSITE™ provided by Halliburton Energy Services, Inc. Any suitable control system or interface may be used in keeping with the principles of this disclosure.

In certain embodiments, the control system may be communicatively coupled to an external communications interface. The external communications interface may permit the data from the control system to be remotely accessible (i.e., from a location other than the well site) by any remote information handling system communicatively coupled to the external communications interface via, for example, a satellite, a modem or wireless connections. In one embodiment, the external communications interface may include a router.

In accordance with an exemplary embodiment of the present disclosure, once feeds from one or more sensors are obtained, they may be combined and used to identify various metrics. For instance, if there is data that deviates from normal expectancy at the rig site, the combined system may show another reading of the data from another sensor that may help identify the type of deviation. As would be appreciated by those of ordinary skill in the art, with the benefit of this disclosure, a control system may also collect data from multiple rigsites and wells to perform quality checks across a plurality of rigs.

As would be appreciated by those of ordinary skill in the art, with the benefit of this disclosure, one or more information handling systems may be used to implement the methods disclosed herein. In certain embodiments, the different information handling systems may be communicatively coupled through a wired or wireless system to facilitate data transmission between the different subsystems. Moreover, each information handling system may include a computer readable media to store data generated by the subsystem as well as preset job performance requirements and standards.

The systems and methods of the present disclosure may be used to monitor or characterize fluids and/or subterranean formations in conjunction with any subterranean operation involving the applicable equipment. For example, the systems and methods of the present disclosure may be used in cementing operations, stimulation operations (e.g., fracturing, acidizing, etc.), completion operations, remedial operations, drilling operations, and the like. A person of skill in the art, with the benefit of this disclosure, will recognize how to apply or implement the systems and methods of the present disclosure as disclosed herein in a particular operation.

An embodiment of the present disclosure is a fluid monitoring and control system including: an information handling system; one or more fluid measurement devices communicatively coupled to the information handling system that are configured to detect the volume or flow rate of one or more fluids introduced into or exiting a well bore; a gas injection apparatus that is configured to introduce one or more noble gases into a fluid or the well bore; a gas extraction system that is configured to extract one or more gaseous samples from one or more fluids exiting the well bore; and a gas analyzer communicatively coupled to the information handling system that is configured to receive one or more gaseous samples from the gas extraction system; wherein the information handling system is configured to receive data from the gas analyzer regarding the presence of the one or more noble gases in the gaseous samples and data from the one or more fluid measurement devices regarding the volume or flow rate of one or more fluids introduced into or exiting the well bore; and wherein the information handling system is configured to use data received from the gas analyzer and the one or more fluid measurement devices to determine one or more parameters selected from the group consisting of: the total volume of the well bore, a lag time in the well bore, a flow characteristic in the well bore, the efficiency of the gas extraction system, and any combination thereof. Optionally, the information handling system is configured to determine a flow characteristic in the well bore selected from the group consisting of turbulent flow, laminar flow, and any combination thereof. Optionally, the information handling system is further configured to determine the one or more parameters based at least in part on one or more of the following: the relative times at which the first and second quantities of one or more noble gases are provided in the fluid or detected, and the quantity of the one or more noble gases detected in the portion of the fluid that has been circulated in a portion of the well bore. Optionally, the information handling system is configured to use data received from the gas analyzer and the one or more fluid measurement devices to determine the total volume of the well bore, a lag time in the well bore, and the efficiency of the gas extraction system. Optionally, the information handling system is configured to use data received from the gas analyzer and the one or more fluid measurement devices to determine the total volume of the well bore, a lag time in the well bore, and the efficiency of the gas extraction system substantially simultaneously. Optionally, the information handling system is configured to determine the one or more parameters substantially in or near real time. Optionally, the one or more noble gases consists essentially of a single noble gas. Optionally, the one or more noble gases include a mixture of noble gases. Optionally, the system further includes an external communications interface communicatively coupled to the information handling system that is configured to permit a remote information handling system communicatively coupled to the external communications interface to access the data received by or stored in the information handling system.

Another embodiment of the present disclosure is a method for monitoring a well bore penetrating a subterranean formation, the method including: providing (100) a first quantity of one or more noble gases of a known volume; circulating (102) at least a portion of the fluid and the one or more noble gases in a portion of the well bore; detecting (104) a second quantity of the one or more noble gases in a portion of the fluid that has been circulated in a portion of the well bore; and determining (106) one or more parameters relating to the well bore based at least in part on one or more of the following: the relative times at which the first and second quantities of one or more noble gases are provided or detected, and the quantity of the one or more noble gases detected in the portion of the fluid that has been circulated in a portion of the well bore, and wherein the one or more parameters relating to the well bore are selected from the group consisting of: the total volume of the well bore, a lag time in the well bore, a flow characteristic in the well bore, and any combination thereof. Optionally, providing a first quantity of one or more noble gases of a known volume includes introducing the first quantity of the one or more noble gases into the fluid, and recording the time at which the first quantity of one or more noble gases is introduced into the fluid. Optionally, determining one or more parameters relating to the well bore includes determining the total volume of the well bore, a lag time in the well bore, and the efficiency of the gas extraction system. Optionally, determining a flow characteristic in the well bore selected from the group consisting of turbulent flow, laminar flow, and any combination thereof. Optionally, the fluid includes a drilling fluid. Optionally, the one or more parameters relating to the well bore are determined substantially in or near real time. Optionally, the method further includes accessing data regarding the one or more parameters, the time at which a quantity of one or more noble gases is provided or detected, the quantity of the one or more noble gases detected in the portion of the fluid that has been circulated in a portion of the well bore, or any combination thereof from a remote location.

Another embodiment of the present disclosure is a method for determining the efficiency of a gas extraction system used to process samples of fluids circulated in a well bore penetrating a subterranean formation, the method including: providing (100) a first quantity of one or more noble gases of a known volume; circulating (102) at least a portion of a fluid and the one or more noble gases in a portion of the well bore; using the gas extraction system to extract one or more gaseous samples from the portion of the fluid; detecting (104) a second quantity of the one or more noble gases in the one or more gaseous samples; and determining (106) the efficiency of the gas extraction system based at least in part on the ratio of the second quantity of the one or more noble gases detected in the one or more gaseous samples to the first quantity of the one or more noble gases provided in the fluid. Optionally, the fluid includes a drilling fluid. Optionally, the efficiency of the gas extraction system is determined substantially in or near real time. Optionally, the method further includes accessing data regarding the efficiency of the gas extraction system, a quantity of the one or more noble gases detected in one or more gaseous samples, a quantity of the one or more noble gases provided, or any combination thereof from a remote location.

Therefore, the present disclosure is adapted to carry out the claimed methods and systems. While the disclosure has been depicted and described by reference to exemplary embodiments of the disclosure, such a reference does not imply a limitation on the disclosure, and no such limitation is to be inferred. The disclosure is capable of considerable modification, alteration, and equivalents in form and function, as will occur to those ordinarily skilled in the pertinent arts and having the benefit of this disclosure. The depicted and described embodiments of the disclosure are exemplary only, and are not exhaustive of the scope of the disclosure. Consequently, the disclosure is intended to be limited only by the scope of the appended claims, giving full cognizance to equivalents in all respects. The terms in the claims have their plain, ordinary meaning unless otherwise explicitly and clearly defined by the patentee.

What is claimed is:

1. A fluid monitoring and control system comprising:
an information handling system;
one or more fluid measurement devices communicatively coupled to the information handling system that are configured to detect volume or flow rate of one or more fluids introduced into or exiting a well bore;
a gas injection apparatus that is configured to introduce one or more noble gases into a fluid of the one or more fluids or the well bore;
a gas extraction system that is configured to extract one or more gaseous samples from a portion of the one or more fluids exiting the well bore; and
a gas analyzer communicatively coupled to the information handling system that is configured to receive one or more gaseous samples from the gas extraction system;
wherein the information handling system is configured to receive data from the gas analyzer regarding the presence of the one or more noble gases in the gaseous samples and data from the one or more fluid measurement devices regarding the volume or flow rate of the one or more fluids introduced into or exiting the well bore; and
wherein the information handling system is configured to use data received from the gas analyzer and the one or more fluid measurement devices to determine one or more parameters selected from the group consisting of: total volume of the well bore, a lag time in the well bore, a flow characteristic in the well bore, efficiency of the gas extraction system, and any combination thereof.

2. The fluid monitoring and control system of claim 1 wherein the information handling system is configured to determine a flow characteristic in the well bore, the flow characteristic being a determination of whether a fluid flow through the well bore is turbulent, laminar, or a combination thereof.

3. The fluid monitoring and control system of claim 1 wherein the information handling system is further configured to determine the one or more parameters based at least in part on one or more of the following: relative times at which first and second quantities of the one or more noble gases are provided in the fluid or detected, and the quantity of the one or more noble gases detected in a portion of fluid that has been circulated in a portion of the well bore.

4. The fluid monitoring and control system of claim 1 wherein the information handling system is configured to use data received from the gas analyzer and the one or more fluid measurement devices to determine the total volume of the well bore, the lag time in the well bore, and the efficiency of the gas extraction system.

5. The fluid monitoring and control system of claim 4 wherein the information handling system is configured to use data received from the gas analyzer and the one or more fluid measurement devices to determine the total volume of the well bore, the lag time in the well bore, and the efficiency of the gas extraction system substantially simultaneously.

6. The fluid monitoring and control system of claim 1 wherein the one or more noble gases consists essentially of a single noble gas.

7. The fluid monitoring and control system of claim 1 wherein the one or more noble gases comprise a mixture of noble gases.

8. The fluid monitoring and control system of claim 1 further comprising an external communications interface communicatively coupled to the information handling system that is configured to permit a remote information handling system communicatively coupled to the external communications interface to access the data received by or stored in the information handling system.

9. A method for monitoring a well bore penetrating a subterranean formation, the method comprising:
providing a first quantity of one or more noble gases of a known volume;
circulating at least a portion of a fluid and the first quantity of one or more noble gases in a portion of the well bore;
detecting a second quantity of the one or more noble gases in a portion of the fluid that has been circulated in a portion of the well bore; and
determining one or more parameters relating to the well bore based at least in part on one or more of the following:
relative times at which the first and second quantities of the one or more noble gases are provided or detected, and
the quantity of the one or more noble gases detected in the portion of the fluid that has been circulated in a portion of the well bore,
wherein the one or more parameters relating to the well bore are selected from the group consisting of: total volume of the well bore, a lag time in the well bore, a flow characteristic in the well bore, and any combination thereof; and
wherein determining the one or more parameters relating to the well bore comprises using a gas extraction system that is configured to extract one or more gaseous samples from at least a portion of the fluid that has been circulated in a portion of the well bore.

10. The method of claim 9 wherein providing a first quantity of one or more noble gases of a known volume comprises:
introducing the first quantity of the one or more noble gases into the fluid; and
recording the time at which the first quantity of one or more noble gases is introduced into the fluid.

11. The method of claim 9 wherein determining one or more parameters relating to the well bore comprises determining the total volume of the well bore, a lag time in the well bore, and the efficiency of the gas extraction system.

12. The method of claim 9 further comprising determining a flow characteristic in the well bore, the flow characteristic being a determination of whether a fluid flow through the well bore is turbulent, laminar, or a combination thereof.

13. The method of claim 9, further comprising:
performing a drilling operation on the well bore; and
circulating the portion of the fluid and the first quantity of one or more noble gases in the portion of the well bore during the drilling operation, wherein the fluid comprises a drilling fluid.

14. The method of claim 9 wherein the one or more parameters relating to the well bore are determined substantially in or near real time.

15. The method of claim 9 further comprising accessing data regarding the one or more parameters, the time at which a quantity of one or more noble gases is provided or detected, the quantity of the one or more noble gases detected in the portion of the fluid that has been circulated in a portion of the well bore, or any combination thereof from a remote location.

16. A method for determining the efficiency of a gas extraction system used to process samples of fluids circulated in a well bore penetrating a subterranean formation, the method comprising:

providing a first quantity of one or more noble gases of a known volume;

circulating at least a portion of a fluid and the one or more noble gases in a portion of the well bore;

using the gas extraction system to extract one or more gaseous samples from the portion of the fluid;

detecting a second quantity of the one or more noble gases in the one or more gaseous samples; and determining the efficiency of the gas extraction system based at least in part on the ratio of the second quantity of the one or more noble gases detected in the one or more gaseous samples to the first quantity of the one or more noble gases provided in the fluid.

17. The method of claim 16 wherein the fluid comprises a drilling fluid.

18. The method of claim 16 wherein the efficiency of the gas extraction system is determined substantially in or near real time.

19. The method of claim 16 further comprising accessing data regarding the efficiency of the gas extraction system, a quantity of the one or more noble gases detected in one or more gaseous samples, a quantity of the one or more noble gases provided, or any combination thereof from a remote location.

20. The fluid monitoring and control system of claim 1, wherein the one or more parameters are selected from the group consisting of: the total volume of the well bore, the lag time in the well bore, the efficiency of the gas extraction system, and any combination thereof.

\* \* \* \* \*